(12) United States Patent
Karl et al.

(10) Patent No.: US 6,210,975 B1
(45) Date of Patent: Apr. 3, 2001

(54) PROCESS FOR DETERMINING A BINDABLE ANALYTE VIA IMMUNE PRECIPITATION AND REAGENT THEREFOR

(75) Inventors: Johann Karl, Peissenberg; Fridl Lang, Tutzing, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 07/771,097

(22) Filed: Oct. 4, 1991

(30) Foreign Application Priority Data

Oct. 30, 1990 (DE) ................................. 40 34 509

(51) Int. Cl.⁷ ...................... G01N 33/543; G01N 33/546; G01N 33/539; G01N 33/53

(52) U.S. Cl. .................... 436/518; 436/533; 436/534; 436/539; 436/824; 435/7.1

(58) Field of Search ................................. 436/519, 518, 436/826, 533, 534, 539, 824; 435/7.1; 530/387.1

(56) References Cited

U.S. PATENT DOCUMENTS

| | | | |
|---|---|---|---|
| 3,880,988 | 4/1975 | Fly | 424/11 |
| 4,298,592 | * 11/1981 | Lin et al. | 424/1 |
| 5,102,788 | * 4/1992 | Cole | 435/7.9 |

FOREIGN PATENT DOCUMENTS

| | | |
|---|---|---|
| 0148463 | 12/1989 | (EP). |
| 2062224 | * 5/1981 | (GB). |
| 0002660 | * 1/1983 | (JP). |
| 582660 | 3/1983 | (JP). |
| 01104198 | 8/1983 | (JP). |
| 02257063 | 10/1990 | (JP). |
| WO8502258 | 5/1985 | (WO). |
| WO8900694 | 1/1989 | (WO). |

OTHER PUBLICATIONS

Atha et al., *J. Biol. Chem.* 256(23): 12108–12117 (1981).*
Sigma Catalog, pp. 494–495, 1194, 1006 (1988).*
Hellsing, K., et al., "Enhancing Effects of Nonionic Polymers on Immunochemical Reactions," in *Automated Immunoanalysis*, (Marcel Decker, NY), pp. 67–112, 1977.*

* cited by examiner

*Primary Examiner*—Yvonne Eyler
*Assistant Examiner*—Jennifer Nichols
(74) *Attorney, Agent, or Firm*—Fulbright & Jaworski (57) ABSTRACT

The invention involves methods for determining analytes, and reagents for use in these methods. The methods and reagents use one or both of a polyvinyl/pyrolidone with a molecular weight of at least 360,000, and a polyethylene glycol with molecular weight of at least 40,000. The assays are carried out nephelometrically, or turbidometrically. The reagents include at least one antibody which binds the analyte. The hook effect is reduced or avoided in the practice of the invention.

19 Claims, 8 Drawing Sheets

PROCESS FOR DETERMINING A BINDABLE ANALYTE VIA IMMUNE PRECIPITATION AND REAGENT THEREFOR

The present invention is concerned with an immunological precipitation process for the determination of a bindable analyte by incubation of a sample solution, which contains the analyte, with a specific receptor bindable with the analyte, as well as a reagent suitable therefor.

Immunological precipitation processes have long been used for the determination of bindable analytes. Use is made of the fact that many immunological reactions lead to formation of molecule aggregates or, in the case of an agglutination reaction, to particle aggregates, which differ considerably in the manner in which these diffuse light as compared to the starting materials. The concentration of these particles can be determined via of this property. For the quantitative determination of analytes, light scattering of particles present in a homogeneous medium, is used to measure the diffused light intensity (nephelometry) and to measure the loss of intensity of a light beam passing through the medium (turbidimetry).

Figure 1:
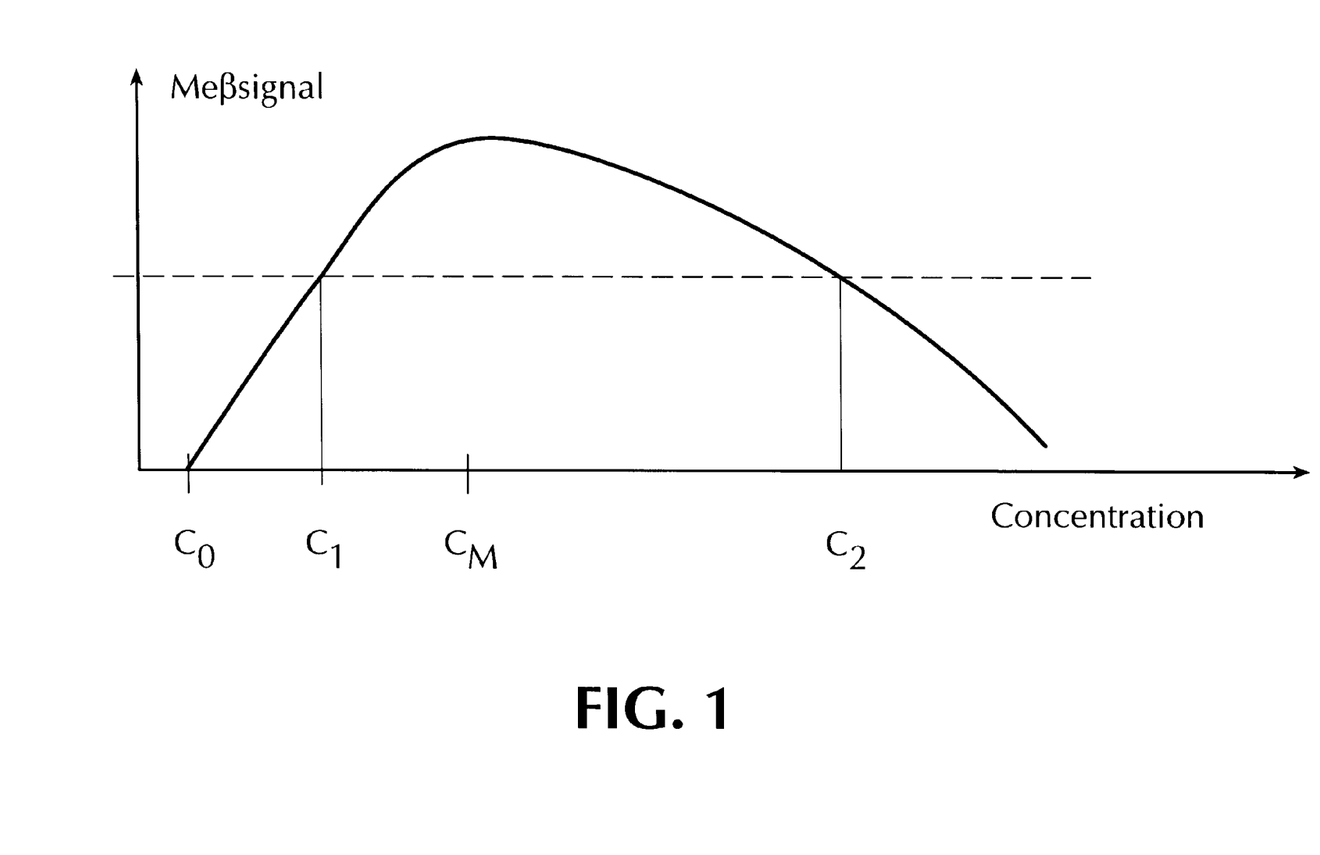
FIG. 1 shows a general Heidelberger curve

A fundamental problem of all quantitative immunological precipitation processes results from the shape of the reaction curve. If antibody concentration is kept constant and increased amounts of antigen are added, then a typical curve results for precipitation (Heidelberger curve) (see FIG. 1 of the accompanying drawings). In the zone of antibody excess, the concentration of the precipitate and thus the measurement signal increases. If further antibody is added the curve passes through a maximum and again decreases in the zone of the antigen excess. Based on this a measurement signal can be associated to two antigen concentration values. If the antibody is present in excess ($C_2$), the measurement signal lies within the measurement range ($C_{0-CM}$) for which the ascending limb of the Heidelberger curve is suitable, then the false antigen concentration $C_1$ is read off. In the case of immunological methods of determination, this effect is also referred to as the "high dose Hook effect", hereinafter briefly referred to as the "Hook effect". For many analytes and especially proteins, the naturally occurring maximum physiological concentration lies far beyond the maximum of the Heidelberger curve so that these possibilities of error occur very frequently. In order to avoid these errors when determining the analyte it must be ascertained whether the measurement signal is present in the ascending or descending limb of the Heidelberger curve.

The oldest and most certain method was described by H. E. Schulze and G. Schwick, Prot. Biol. Fluids, 5, 15–25/1958, which provides for a double determination with two different sample dilutions. In the case of antigen excess, with the more highly diluted sample, a greater measurement signal is obtained than with the more concentrated sample.

An improved embodiment of this process provides for further addition of antibodies. When an excess of antigen is present a signal increase occurs (T. O. Tiffany et al., Clin. Chem. 20, 1005–1061/1974). By additional pipetting of antigen material of known concentration, antigen excess can also be recognized (J. C. Sternberg, Clin. Chem. 23, 1456–1464/1977).

Furthermore, several processes have been described which seek to recognize the hook effect by laborious computer-controlled evaluations. By determination of the period of reaction up to the appearance of the maximum reaction velocity for nephelometric measurements, it is possible to discriminate between antigen and antibody excess (DE-A-27 24 722; EP-B-0,148,463).

These processes all suffer from the disadvantage that either an additional pipetting step or computer-controlled evaluation is necessary and, in the case of automation, this automatically leads to an increase of the cost of the apparatus. A better alternative for avoiding erroneous interpretations in immunological precipitation processes would be to change the form of the Heidelberger curve so that, after the maximum, a plateau is reached and the appearance of the hook effect is completely avoided or is displaced into an antigen concentration range which no longer occurs under physiological conditions.

In U.S. Pat. No. 4,595,661 sandwich and nephelometric immunoassays are described which use highly specific antibodies and reagents normally present in an immunoassay, and also contain at least one further low-affinity antibody against the analyte in order to reduce the hook effect. The disadvantage of this process is obvious since, for each analyte to be detected, two specific antibodies with different affinities for the analyte must be prepared.

Therefore, it is an object of the present invention to provide a simple immunological precipitation process for the determination of a bindable analyte which avoids the hook effect.

Thus, according to the present invention, there is provided an immunological precipitation process for the determination of a bindable analyte by incubation of a sample solution which contains the analyte with a specific receptor bindable with the analyte, wherein to the test solution is added a non-ionic polymer from the group consisting of dextran having a molecular weight of at least 200,000, polyvinylpyrrolidone having a molecular weight of at least 100,000 and polyethylene glycol with a molecular weight of at least 10,000.

The present invention also provides a reagent for carrying out an immunological precipitation process for the determination of a bindable analyte in a sample solution, wherein, in addition to the materials necessary for the immunological precipitation process, it contains a non-ionic polymer from the group comprising dextran with a molecular weight of at least 200,000, polyvinylpyrrolidone with a molecular weight of at least 100,000 and polyethylene glycol with a molecular weight of at least 10,000.

The non-ionic polymer concentration in the test batch, i.e. the mixture of the sample solution, the specific receptor and the non-ionic polymer, is at least 1% by weight. Below this concentration, the action according to the present invention is no longer achieved. The upper amount is given by the appearance of non-specific turbidities resulting from high polymer concentrations. In the test batch, a non-ionic polymer concentration of 2 to 6% by weight has proved to be advantageous, a concentration of from 3 to 4% by weight being especially preferred. The reagent according to the present invention can be present as powder, lyophilisate or solution.

As non-ionic polymers, there e.g. polyethylene glycol, polyvinyl pyrrolidone or dextran can be used. Non-ionic polymers are obtainable in differing degrees of polymerisation, i.e. with different molecular weights. For the present invention, high molecular weight non-ionic polymers are preferred, the upper limit of the molecular weight depending upon the molecular weight at which the polymer is no longer sufficiently soluble in the test batch in order to be effective according to the present invention. For use in the process according to the present invention, polyethylene glycol has a molecular weight of at least 10,000, preferably a molecular weight of from 10,000 and 300,000 and most preferably a molecular weight of 40,000. Polyvinylpyrrolidone has a molecular weight of at least 100,000 and preferably of 360,000 to 750,000. Dextran is preferably used which has molecular weight of at least 200,000. Especially preferred is dextran with a molecular weight of from 500,000 to 1,000,000.

It was known to add polymers, such as polyethylene glycol, dextran or hyaluronic acid to immunological precipitation processes in order to increase the sensitivity and to accelerate reactions. Polyethylene glycol with a molecular weight of about 6000 is usually employed in a concentration of approximately 4% by weight in the case of nephelometric or turbidimetric determinations of an immunological precipitation reaction for these purposes (EP-B-0,148,463).

It was surprising that the addition of non-ionic polymers with the said molecular weights and concentrations avoids the hook effect as a disturbance which occurs in the case of high antigen concentrations, i.e. the hook effect is avoided or can be displaced into an antigen concentration range which no longer occurs under physiological conditions. At the same time via adding the aformentioned materials, the sensitivity and velocity of the immunological precipitation reaction is increased, often beyond that which is achieved by the otherwise usual addition of polyethylene glycol having a molecular weight of 6000. Thus, the addition of polyethylene glycol having a molecular weight of 6000 is no longer necessary in the process according to the present invention. In the case of the process according to the present invention, a false antigen concentration can no longer be measured since, as antigen concentration increases, the measurement signal, after passing the maximum of the precipitation curve, no longer decreases so strongly or only decreases to the part where it again comes to lie in the usual measurement range at a non-physiologically possible high antigen concentration. A discrimination between the ascending and descending limb of the Heidelberger curve, which previously required an additional pipetting step or computer-controlled evaluation, is thus unnecessary. The process according to the present invention can be carried out without increased costs, as compared to prior art processes, since the use of the non-ionic polymers of the present invention can replace the polyethylene glycol having a molecular weight of 6000 usually added. In addition, in the case of automated use, the cost of apparatus can be reduced since additional pipetting steps or laborious evaluation can be omitted.

By an immunological precipitation process in the meaning of the present invention is to be understood all reactions between immunological receptors and analytes which lead to turbidity of the test solution resulting from the formation of the analyte-receptor complex. The turbidity can be strengthened by light-scattering particles to which one component of the immunological reaction, i.e. receptor or analyte or analyte analogue, is or can be bound. In this case, it is an agglutination test. The non-ionic polymer according to the present invention is preferably used in immunological precipitation processes where the turbidity is caused only by analyte receptor complexes and light-scattering particles are not used. Furthermore, immunological precipitation processes is also to be understood to mean immune diffusion processes, and preferably the radial immune diffusion.

The terms analyte and receptor as used herein refers to any and all pairs of substances which are bindable with each other. This is to include, e.g. immunologically bindable substance pairs, as well as substance pairs which behave analogously.

Bindable, specific receptors as used herein include binding components of the analyte to be analysed. As receptor, antibodies or antibody fragments are preferred. These can be both polyclonal and monoclonal antibodies.

By an analyte is to be understood a substance which has at least two epitopes, i.e. binding positions for the specific receptor. The process according to the present invention is especially preferred when the analyte is a protein. The analyte can be present in a body fluid, for example plasma, serum, urine, saliva or the like, or in an appropriate buffer solution. The process according to the present invention is, for example, especially suitable for the determination of albumin in urine, for the determination of apolipoproteins AI and B in serum or plasma and for the determination of immunoglobulins, ferritin, lipoprotein (a) (Lp(a)) and $\alpha$-1-microglobulin. In the case in which the analyte itself is an antibody, the antigen reacting with this antibody or, an anti-antibody directed against this antibody can be used as specific receptor.

The measurement of the turbidity in the case of the immunological precipitation process according to the present invention can take place with appropriate apparatus not only nephelometrically but also turbidimetrically. The determination of the concentration of the analyte in the sample takes place by comparison with a standard of known analyte concentration.

By "a reagent for carrying out the immunological precipitation process for the determination of a bindable analyte in a sample solution", there is to be understood a composition which, in addition to the materials necessary for the immunological precipitation process, for example adjuvants, buffer substances or, in the case of an agglutination test, particles coated with a binding component, preferably latex particles, also contains a non-ionic polymer which is effective according to the present invention.. The concentration of this non-ionic polymer in the reagent is thereby to be so chosen that, in the test batch, i.e. after addition of the sample to the reagent, the end concentration of the polymer is at least 1 and preferably 2 to 6% by weight.

The following examples are given for the purpose of illustrating the present invention:

EXAMPLE 1

Determination of Human Albumin in Urine

In urine diagnosis, the determination of albumin is an important criterion for the assessment of kidney damage. The normal value of albumin in urine is from 10 to 20 mg/l but physiological concentrations of up to 20,000 mg/l are possible. For the avoidance of erroneous interpretations, the hook effect should be completely avoided in the case of albumin determinations or displaced into the concentration range above 20,000 mg/l. As a rule, the normal measurement range in the case of turbidometric determinations only extends up to an albumin concentration of 300 mg/l.

The carrying out of the experiment, as well as the reagents employed, are the same in the following examples with the exception of the addition of the non-ionic polymer for the avoidance of the hook effect as disturbance:
Solution 1 (reaction buffer)
  50 mmol/l Tris, pH 8.0
  1% by weight non-ionic detergent
  0.1% by weight sodium azide
To solution 1 were added the non-ionic polymers or, as comparison with the process of the prior art, PEG 6000 in concentrations such that, in the test batch, there is achieved the particular given end concentration.
Solution 2 (antiserum)
  100 mmol/l Tris, pH 7.2
  100 mmol/l sodium chloride
  0.1% by weight sodium azide
  15 mg/ml polyclonal anti-human serum albumin sheep antibody (PAB<HSA>S-IgG)
Solution 3 (calibrator)
  50 mmol/l phosphate buffer, pH 8.0
  100 mmol/l sodium chloride
  0.1% by weight sodium azide
  0 to 20,000 mg/l human albumin (HSA)

The measurements were carried out bichromatically at a wavelength of 340 nm (correction wavelength 700 nm) on a Hitachi 704 of Boehringer Mannheim GmbH, Germany, at a temperature of 37° C. 20 μl of solution 3 were mixed with 350 μl of solution 1 and incubated for 5 minutes. Thereafter, the first measurement of the extinction took place (E1). 70 μl of solution 2 were pipetted thereto and the test batch incubated for a further 5 minutes. Thereafter, a further extinction measurement (E2) took place. For the evaluation of the results, the extinction difference ΔE=E2−E1 was plotted against the albumin concentration.

1.1 Avoidance of the hook effect by the addition of polyethylene glycol 1.1.1 Comparison between the process of the prior art (addition of PEG 6000) and the process according to the present invention (addition of PEG 40,000)

To solution 1 was added PEG 6000 or PEG 40,000 in such concentrations that, in each case, an end concentration of 4% by weight was achieved in the test batch. The test was carried out as described under "1".

Figure 2:
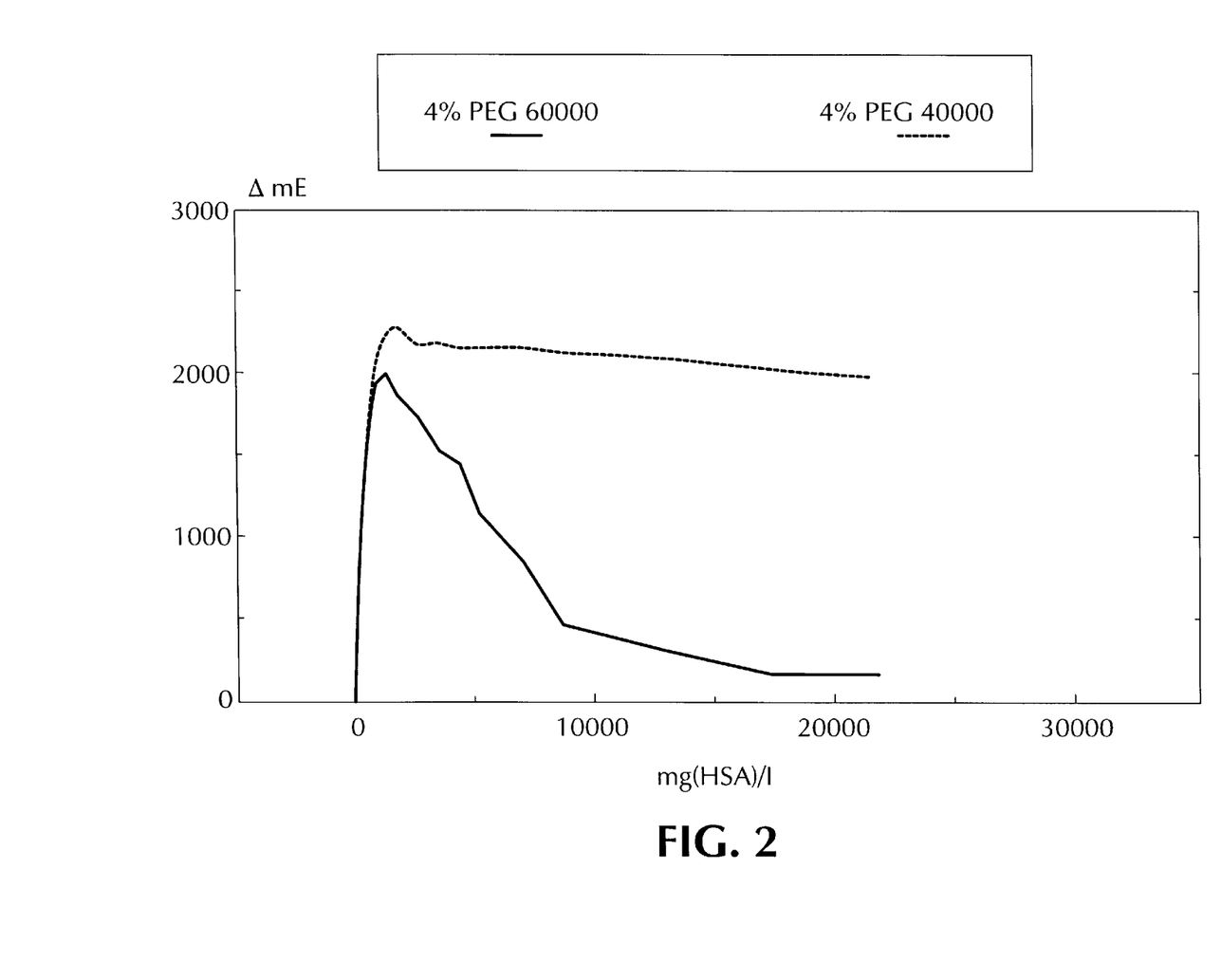
FIG. 2 shows avoidance of the hook effect in an assay, in accordance with the invention.

In the case of the process of the prior art, i.e. the addition of PEG 6000, the hook effect took place in the case of albumin concentrations above the measurement range which extended to about 400 mg/l HSA. In the case of the addition according to the present invention of PEG 40,000, with HSA concentrations above the measurement range, no significant decrease of the extinction resulted. Up to an HSA concentration of about 20,000 mg/l, which is possible under physiological conditions, the hook effect is avoided as disturbance (see FIG. 2 of the accompanying drawings). Furthermore, it was shown that the process according to the present invention led to an acceleration of the reaction and to an increase of the sensitivity of the immunological precipitation process which extended beyond the measure that is achieved by the process of the prior art.

1.1.2 Influence of the concentration of PEG 40,000

PEG 40,000 was added to solution 1 in different concentrations. The end concentration in the test batch was from 0 to 6% by weight. The use of still higher concentrations is of no value since above 6% by weight of PEG 40,000, non-specific turbidities occur which prevent an exact measurement.

Figure 3:
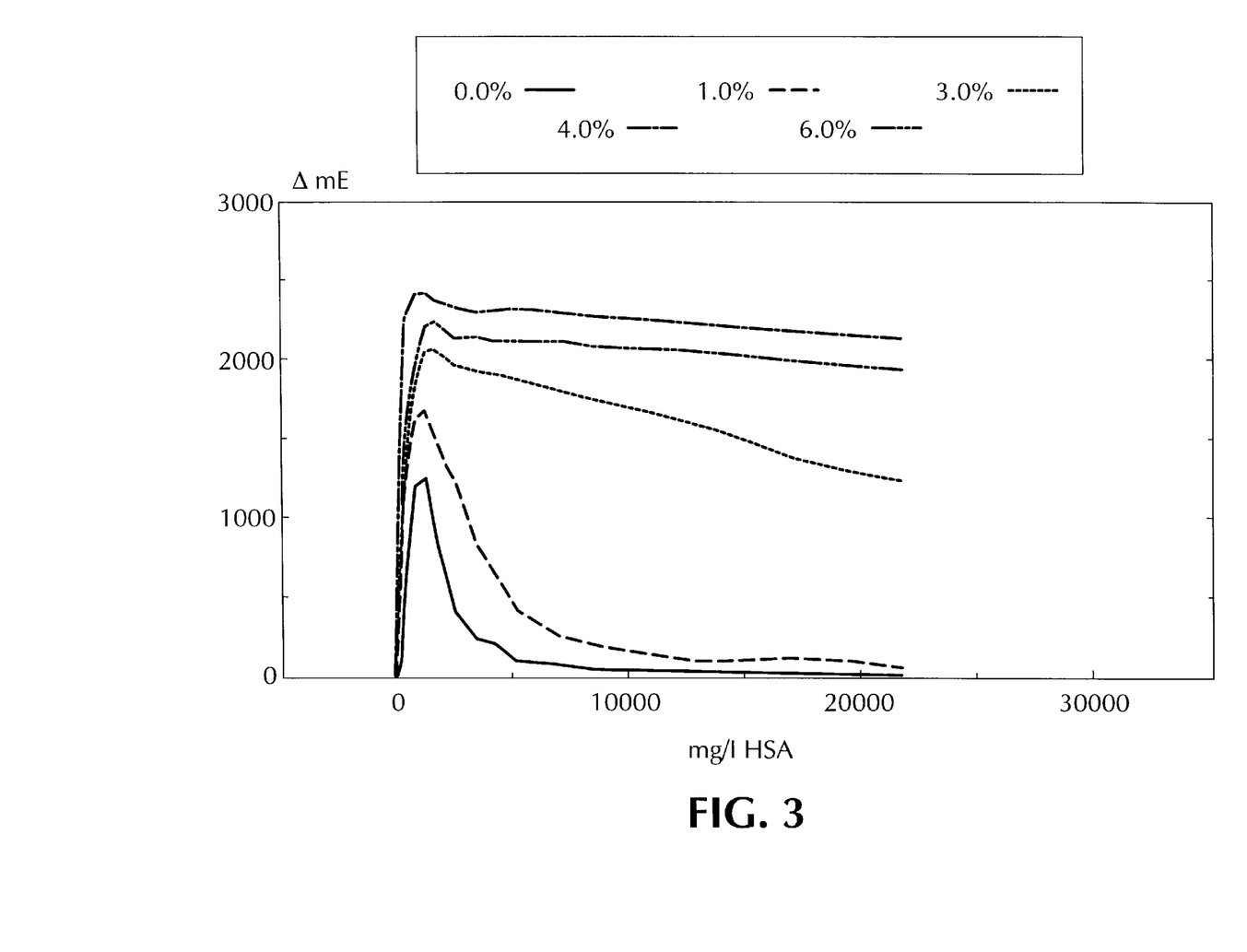
FIG. 3 shows occurrence of the hook effect using low concentrations of PEG 40,000 when by weight.

In the case of PEG 40,000 concentrations of up to 1% by weight, the hook effect occurred above HSA concentrations of 400 mg/l (see FIG. 3 of the accompanying drawings). Above 1% by weight of PEG 40,000 a distinct decrease of the hook effect was obtained in comparison with the method of the prior art (4% by weight PEG 6000, the values are not graphically shown in FIG. 3). From these results, it can be seen that the non-ionic polymer according to the present invention can be used in concentrations of at least 1 and preferably of 2 to 6% by weight and, in an especially preferred embodiment 3 to 4% by weight.

1.1.3 Influence of the molecular weight of polyethylene glycol

In order to determine the influence of the molecular weight of PEG on the immunological precipitation, polymers with different degrees of polymerisation were used. PEG with molecular weights of 2000, 6000, 10,000, 40,000 and 300,000 were tested. The particular concentration in the test batch was uniformly 4% by weight.

Figure 4:
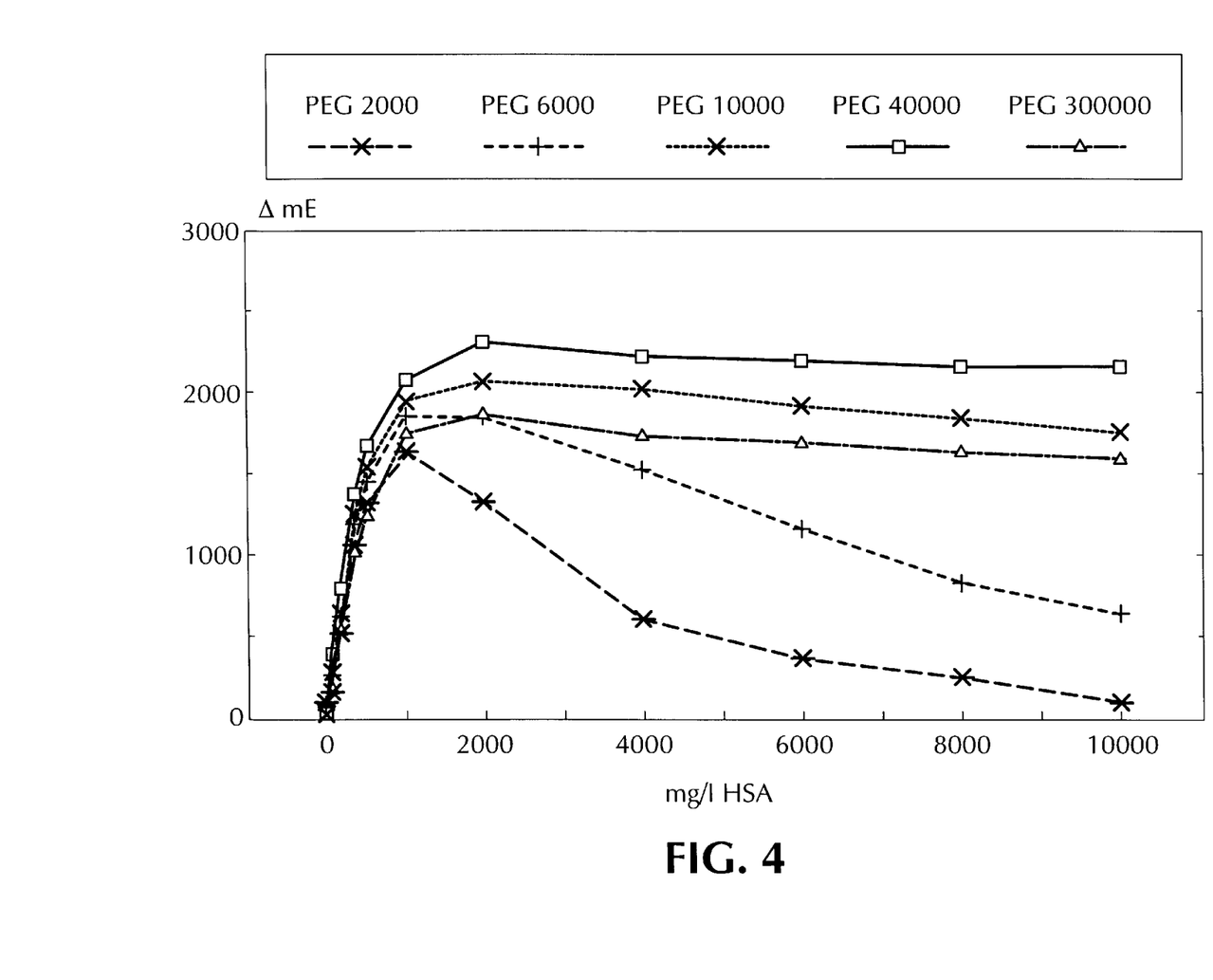
FIG. 4 shows the influence of the molecular weight of PEG on reducing hook effect.

Of from the molecular weight of 10,000, the hook effect was avoided. Preferably PEG with a molecular weight of 40,000 (see FIG. 4 of the accompanying drawings) is used.

1.2 Determination of albumin in urine with the addition of dextran

As in the case of Example 1.1.3, the influence of the molecular weight of a different non-ionic polymer, i.e. dextran, in the process of the present invention was determined in assaying albumin in urine. In each case, the concentration of the dextrans in the test batch was 4% by weight.

Figure 5:
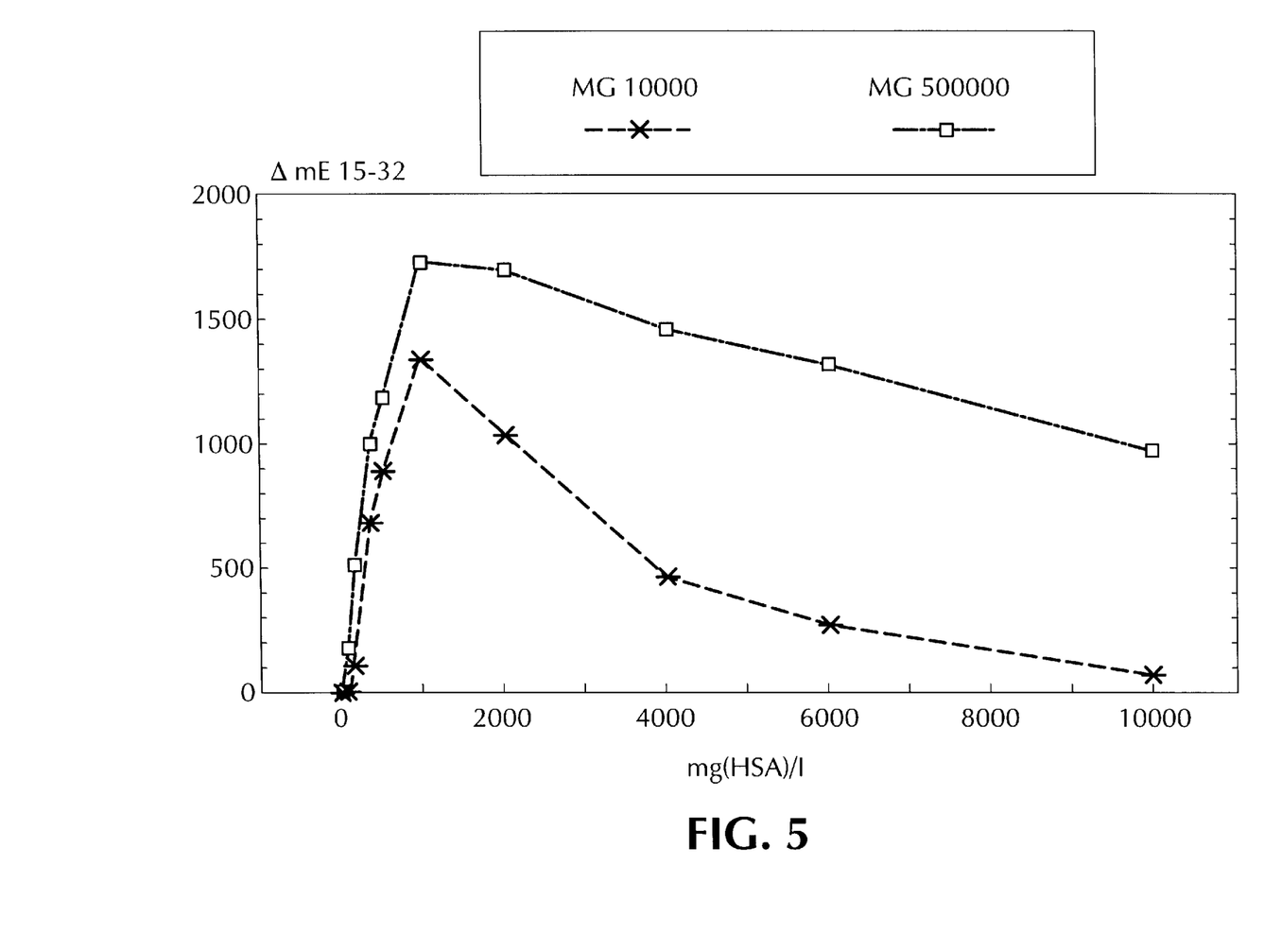
FIG. 5 shows the effect of dextran at varying molecular weights on hook effect.

Of from a molecular weight of 200,000, dextran can be used as additive to avoid the hook effect. Dextrans with a lower molecular weight do not achieve the action according to the present invention (see FIG. 5 of the accompanying drawings).

1.3 Determination of albumin in urine by adding PVP

Using the example of albumin determination, the influence of the molecular weight of polyvinyl pyrrolidone (PVP) on the process according to the present invention was determined. PVP was, in each case, used in an end concentration of 4% by weight, referred to the test batch.

Figure 6:
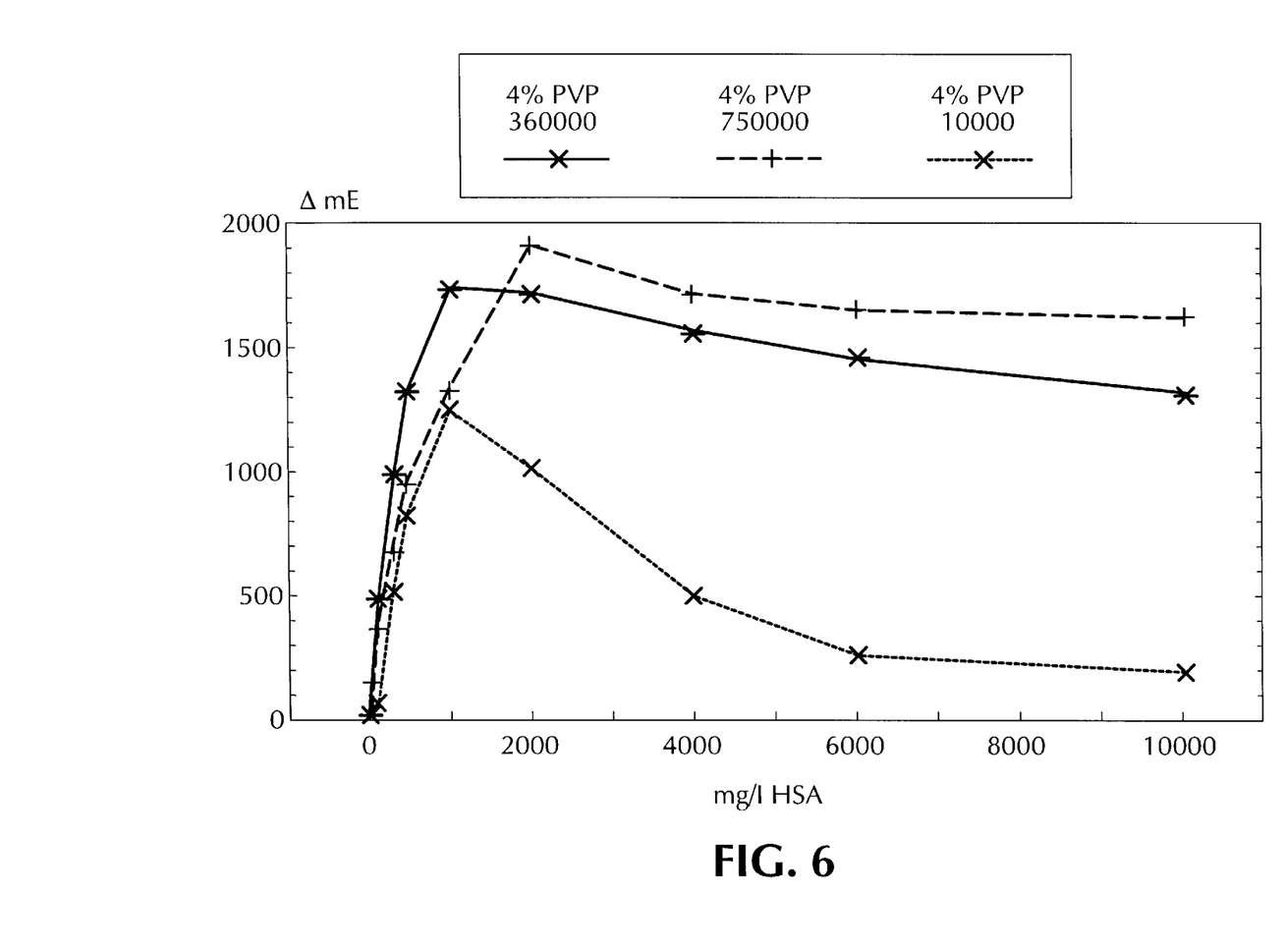
FIG. 6 shows the influence of the molecular weight on reduction of the hook effect by polyvinyl pyrolidone.

Of from a molecular weight of 100,000, PVP can be used to avoid the hook effect. As can be seen from FIG. 6 of the accompanying drawings, preferably PVP with a molecular weight of 360,000 and 750,000 are used.

PVP with a molecular weight of 10,000 does not achieve the action according to the present invention.

EXAMPLE 2

Determination of Apolipoprotein A-I (Apo A-I)

In the case of the determination of the concentration of apolipoprotein A-I, the experiments were carried out as described in Example 1. The measurements were carried out bichromatically at a wavelength of 376 nm (correction wavelength 700 nm) on a Hitachi 704 of Boehringer Mannheim GmbH, Germany, at a temperature of 30° C.

The following reagent solutions were used:
Solution 1 (reaction buffer)
  50 mmol/l Tris, pH 8.0
  1% by weight non-ionic detergent
To the solution PEG 40,000 was added or, as comparison with the process of the prior art, PEG 6000 in such concentrations that an end concentration of 4% by weight was achieved in the test batch.

Solution 2 (antiserum)

Antiserum obtained from Boehringer Mannheim GmbH under the identification number 1381130 and containing polyclonal anti-apolipoprotein A1 sheep antibody (PAB<Apo A1>S-IgG) in 100 mmol Tris, pH 7.2 was used.

Solution 3 (calibrator)

As calibrator, there was used lyophilised human serum obtained from Boehringer Mannheim GmbH under the identification number 1381156 was used.

2 µl of solution 3 were mixed with 350 µl of solution 1 and incubated for 5 minutes. Thereafter, the first extinction measurement took place (E1). 140 µl of solution 2 were pipetted thereto, the test batch was incubated for a further 5 minutes and a second extinction measurement (E2) was carried out. For the evaluation, the extinction differences ΔE=E433 2–E1 was plotted against the apolipoprotein A-I concentration.

The calibration curve was measured following the package insert (identification No. 1378686) of the Tina-quant® apolipoprotein A-I test kit of Boehringer Mannheim GmbH. The calibrator, which contained 211 mg of apolipoprotein A-I/dl, was diluted with 0.9% by weight sodium chloride solution in different dilution steps. The high apolipoprotein A-I concentrations were achieved by pipetting the undiluted calibrator with comparatively high volumes (2 µl, 4 µl etc.).

Figure 7:
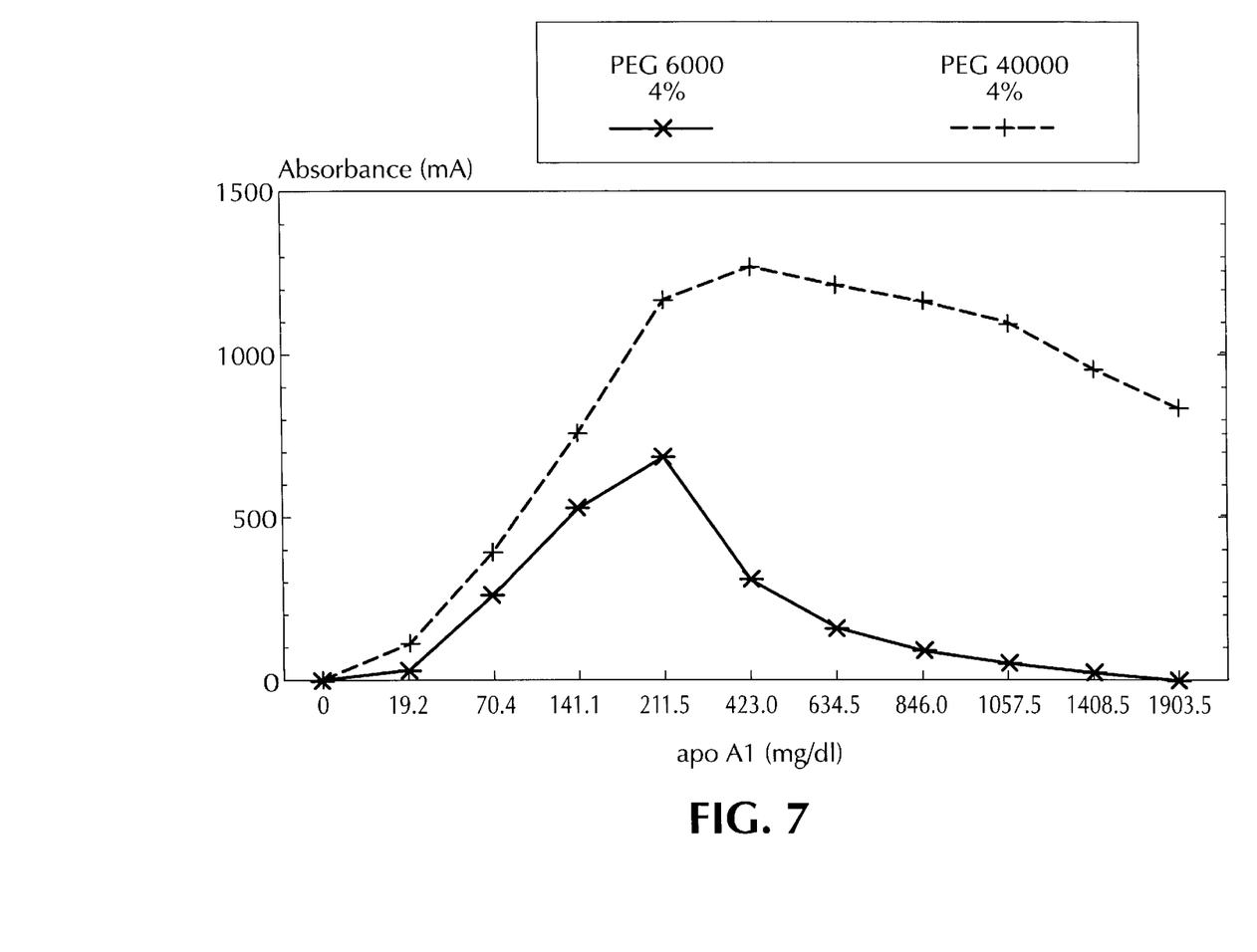
FIG. 7 depicts results obtained when comparing PEG of different molecular weights in an apo-A-I assay.

From FIG. 7 of the accompanying drawings, it can be seen that, using the process according to the prior art, i.e. using PEG having a molecular weight of 6000, a hook effect occurs above an apo-A-I concentration of about 210 mg. Using the present invention, i.e. adding PEG 40,000, the hook effect is displaced into a higher concentration range.

EXAMPLE 3

Determination of α-1-Microglobulin (α-1-M)

The measurements were carried out on a Hitachi 704 as in the preceding Examples. The measurement temperature was 37° C. Measurement was carried out at a wavelength of 340 nm with a correction wavelength of 700 nm.

The following reagent solutions were used

Solution 1 (reaction buffer):

50 mmol/l Tris, pH 8.0

150 mmol/l sodium chloride

1% by weight non-ionic detergent, i.e. PEG 6000 and PEG 40,000, in such concentrations that an end concentration of 4% by weight was achieved in the test batch.

Solution 2 (antiserum)

20 mg/l of polyclonal anti-α-1-microglobulin sheep IgG antibody (PAB<α-1-M>S-IgG) in 50 mmol/l Tris, pH 8.0

Solution 3 (calibrator)

As calibrator, a urine concentrate with an α-1-microglobulin content of 2700 mg/l was used.

Figure 8:
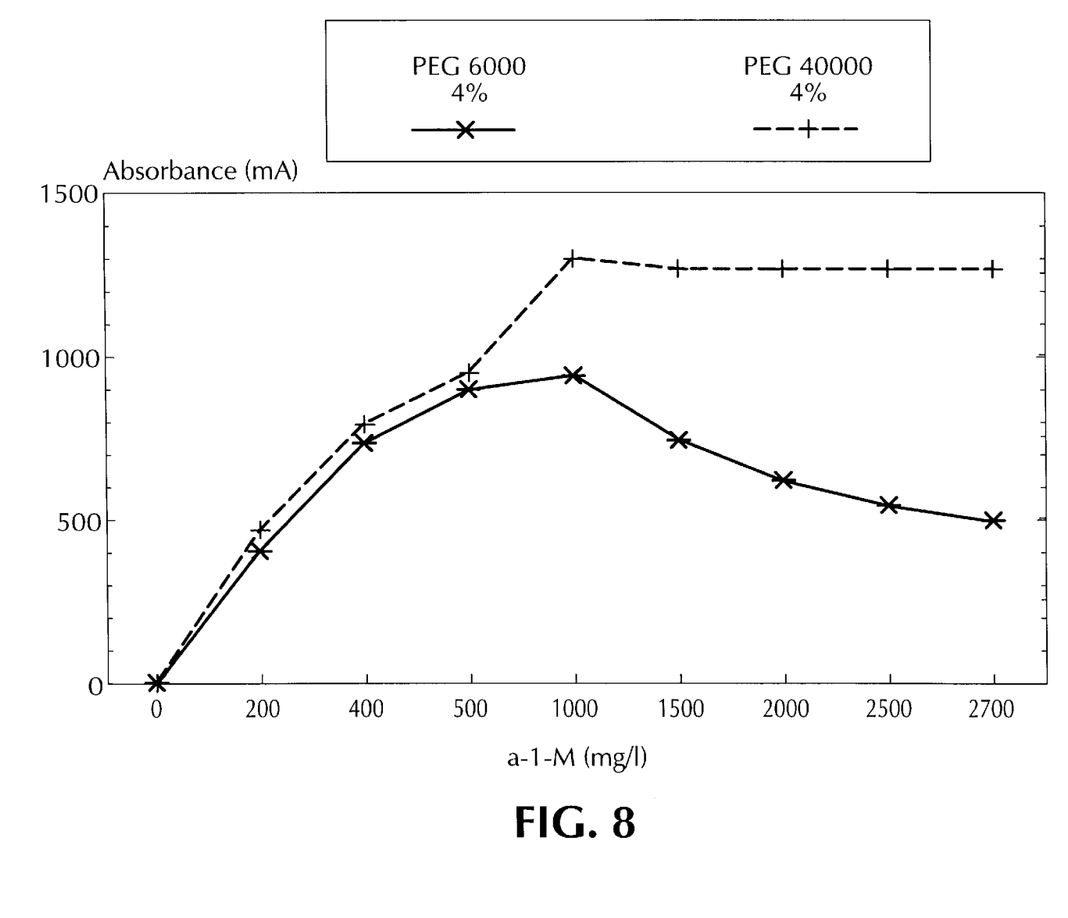
FIG. 8 parallels FIG. 7, but the analyte is $\alpha$-1-microglobulin.

20 µl of solution 3 were mixed with 350 µl of solution 1 and, after 5 minutes, the extinction (E1) was measured. After the addition of 70 µl of solution 2 and incubation for a further 5 minutes, a second extinction (E2) was measured. For the evaluation, the extinction difference ΔE=E2–E1 was plotted (FIG. 8 of the accompanying drawings) against the α-1-M concentration. For the production of a calibration line, the calibrator was diluted in 20 mmol/l of hepes.

Using PEG 6000 (process according to the prior art), a hook effect was observed above an α-1-M concentration of 1000 g/l. Using PEG 40,000, over the whole of the measurement range up to a concentration of 2700 mg/l, no hook effect was observed.

It will be understood that the specification and examples are illustrative but not limitative of the present invention and that other embodiments within the spirit and scope of the invention will suggest themselves to those skilled in the art.

What is claimed is:

1. A method for determining an analyte in a sample solution, said method comprising: contacting said sample solution with a receptor in solution which specifically binds to said analyte to form a precipitate; and quantitatively measuring the amount of formation of said precipitate by a nephelometric or turbidimetric method as a measurement of the amount of said analyte present in said sample solution; said contacting of said sample solution with said receptor being in the presence of at least one non-ionic polymer selected from the group consisting of a polyvinyl pyrrolidone having molecular weight of at least 360,000 and a polyethylene glycol having a molecular weight of at least 40,000.

2. The method of claim 1, wherein said non-ionic polymer is present with said sample solution at a concentration of at least 1% by weight relative to the total weight of said sample solution after contacting with said receptor and said non-ionic polymer.

3. The method of claim 2, wherein said non-ionic polymer is present in an amount ranging from at least 2% to 6% by weight relative to the total weight of said sample solution after contacting with said receptor and said non-ionic polymer.

4. The method of claim 1, wherein said non-ionic polymer is a polyethylene glycol with a molecular weight of at least 40,000.

5. The method of claim 4, wherein said polyethylene glycol has a molecular weight of from about 40,000 to about 300,000.

6. The method of claim 4, wherein said polyethylene glycol has a molecular weight of about 40,000.

7. The method of claim 1, wherein said non-ionic polymer is a polyvinyl pyrrolidone with a molecular weight of at least about 360,000.

8. The method of claim 7, wherein said polyvinyl pyrrolidone has a molecular weight of from about 360,000 to about 750,000.

9. The method of claim 1, wherein said method is an agglutination assay.

10. The method of claim 1, wherein said receptor is a polyclonal antibody.

11. The method of claim 1, wherein said specific receptor comprises at least two different monoclonal antibodies.

12. The method of claim 1, wherein said analyte is a protein.

13. The method of claim 1, wherein said analyte is albumin, apolipoprotein A-I or B, α-1-microglobulin, immunoglobulin, ferritin and lipoprotein (a).

14. Reagent useful in determining an analyte via a precipitation reaction, comprising: a receptor comprising at least one antibody which specifically binds to said analyte to form a precipitate, and at least one non-ionic polymer selected from the group consisting of a polyvinyl pyrrolidone having molecular weight of at least 360,000 and a polyethylene glycol having a molecular weight of at least 40,000.

15. Reagent of claim 14, wherein aid non-ionic polymer is present in an amount equal to at least 1% by weight of a mixture of said receptor, said non-ionic polymer and a sample added thereto.

16. Reagent of claim 15, wherein said non-ionic polymer is present in an amount ranging from about 2 to about 6% by weight of said mixture.

17. A method for determining an analyte in a sample solution, said method comprising:

contacting said sample solution with a receptor in solution, said receptor comprising an antibody which specifically binds to said analyte to form a precipitate; and quantitatively measuring the amount of formation of said precipitate by a nephelometric or turbidimetric method as a measurement of the amount of said analyte present in said sample solution;

said contacting of said sample solution with said receptor being in the presence of at least one non-ionic polymer selected from the group consisting of:

polyvinyl pyrrolidone having a molecular weight of about 360,000 to about 750,000; and polyethylene glycol having a molecular weight of about 40,000 to about 300,000;

said non-ionic polymer being present in an amount constituting from about 2% to about 6% by weight of the combined sample solution, receptor, and polymer.

18. The method of claim 17 and the receptor comprising at least two monoclonal antibodies.

19. The method of claim 17 and the receptor antibody being a polyclonal antibody.

* * * * *